United States Patent
Conti et al.

(10) Patent No.: US 7,621,192 B2
(45) Date of Patent: Nov. 24, 2009

(54) MEDICAL DEVICE DURABILITY TEST APPARATUS HAVING AN INTEGRATED PARTICLE COUNTER AND METHOD OF USE

(75) Inventors: James C. Conti, Galena, MO (US); Elaine R. Strope, Galena, MO (US)

(73) Assignee: Dynatek Laboratories, Inc., Galena, MO (US)

( * ) Notice: Subject to any disclaimer, the term of this patent is extended or adjusted under 35 U.S.C. 154(b) by 343 days.

(21) Appl. No.: 11/494,839

(22) Filed: Jul. 28, 2006

(65) Prior Publication Data
US 2007/0185534 A1 Aug. 9, 2007

Related U.S. Application Data

(60) Provisional application No. 60/704,105, filed on Jul. 29, 2005.

(51) Int. Cl.
*G01N 17/00* (2006.01)
*A61F 2/24* (2006.01)

(52) U.S. Cl. .................. 73/865.6; 623/912; 623/913

(58) Field of Classification Search ............. 73/1.72, 73/37, 168, 865.6, 849, 862; 435/1.2, 284.1, 435/286.5, 297.2, 399, 401; 600/36; 607/119; 623/2.11, 2.13, 912, 913
See application file for complete search history.

(56) References Cited

U.S. PATENT DOCUMENTS

| 4,381,663 | A  | * | 5/1983 | Swanson ................. 73/37 |
| 5,176,153 | A  | * | 1/1993 | Eberhardt .............. 128/897 |
| 5,327,774 | A  | * | 7/1994 | Nguyen et al. ............ 73/37 |
| 5,670,708 | A  | * | 9/1997 | Vilendrer ................. 73/37 |
| 5,792,603 | A  | * | 8/1998 | Dunkelman et al. ....... 435/1.2 |
| 7,254,988 | B2 | * | 8/2007 | Keeble .................. 73/37 |
| 2003/0066338 | A1 | * | 4/2003 | Michalsky et al. ........ 73/37 |
| 2005/0118344 | A1 | * | 6/2005 | Pacetti ................ 427/422 |
| 2005/0119720 | A1 | * | 6/2005 | Gale et al. ............ 623/1.11 |

\* cited by examiner

*Primary Examiner*—David A. Rogers
(74) *Attorney, Agent, or Firm*—Lathop & Gage LLP

(57) ABSTRACT

Apparatuses and methods for determining particle shed rates of implantable or inter-dwelling devices are disclosed. Durability test apparatuses with integrated particle counters produce time-dependent particle shed rate profiles. The apparatuses are designed to accommodate pulsatile flow, resembling a heartbeat at the implantable device. In an embodiment, the pulsatile flow is converted to a steady flow before fluid enters the integrated particle counter.

4 Claims, 2 Drawing Sheets

MEDICAL DEVICE DURABILITY TEST APPARATUS HAVING AN INTEGRATED PARTICLE COUNTER AND METHOD OF USE

RELATED APPLICATIONS

This application claims the benefit of priority to U.S. application No. 60/704,105, filed Jul. 29, 2005, which is incorporated herein by reference.

BACKGROUND

Medical implants are frequently coated with metals, polymers or other materials. Over time, some of these materials may shed small particles that could cause embolic episodes in the cardiovascular system or osteonecrosis in orthopedic applications. Manufacturers of medical implants are required to test the long term durability of their products, for example, to assess structural fatigue. However, current testing requirements do not call for reporting of particle shed rates.

Current technology for determining particle shed rates of implantable medical devices includes running a standard durability test, which for heart-related devices may replicate approximately 400 million heartbeats. The fluid from the test is collected and then filtered with any particles in the fluid being counted. This method suffers from several drawbacks. For example, in tests involving multiple devices, it is impossible to determine which device is shedding. Further, overall particle shed rates may be inaccurate because some medical product coatings are biodegradable and may not survive the testing, which can last several months. Also, these methods do not teach when shedding occurs and may not be precise with regard to shed particle size devolvement, for example, where large particles may become dislodged and then break apart.

SUMMARY

The present instrumentalities overcome the problems outlined above and advance the art by providing apparatuses and methods for determining time-dependent particle shed rates of implantable or inter-dwelling medical devices. Devices that may be tested include, without limitation, heart valves, vascular grafts, vascular stents, nonvascular stents, artificial hearts, catheters, cannulas and orthopedic devices.

In one embodiment, an apparatus for determining a particle shed rate of an implantable medical device includes a pump that moves fluid in contact with the implantable medical device and a particle counter. The particle counter collects data representative of a time-dependent particle shed profile of the implantable medical device. The pump, the implantable medical device, and the particle counter are in fluidic communication. The implantable medical device may be a conduit, or the implantable medical device may be disposed within a conduit.

In one aspect, the pump may apply pulsatile fluid pressure to the device, which may be approximately periodic. A frequency of the periodic fluid pressure may, for example, be from about 50 to 6000 cycles per minute.

In yet another aspect, a method of determining a particle shed rate of an implantable medical device includes deploying the implantable medical device in a durability test apparatus, contacting fluid with the implantable medical device, and analyzing the fluid using an in-line particle counter. The analyzed fluid may further be filtered and recirculated.

In another aspect, a method of determining a time-dependent particle shed profile of an implantable medical device includes deploying the implantable medical device in a durability test apparatus, continuously cycling fluid through the durability test apparatus, which has an in-line particle counter and an in-line filter, and analyzing the fluid with the in-line particle counter over a period of time ranging from about 1 hour to 1 year.

DETAILED DESCRIPTION

Figure 1:
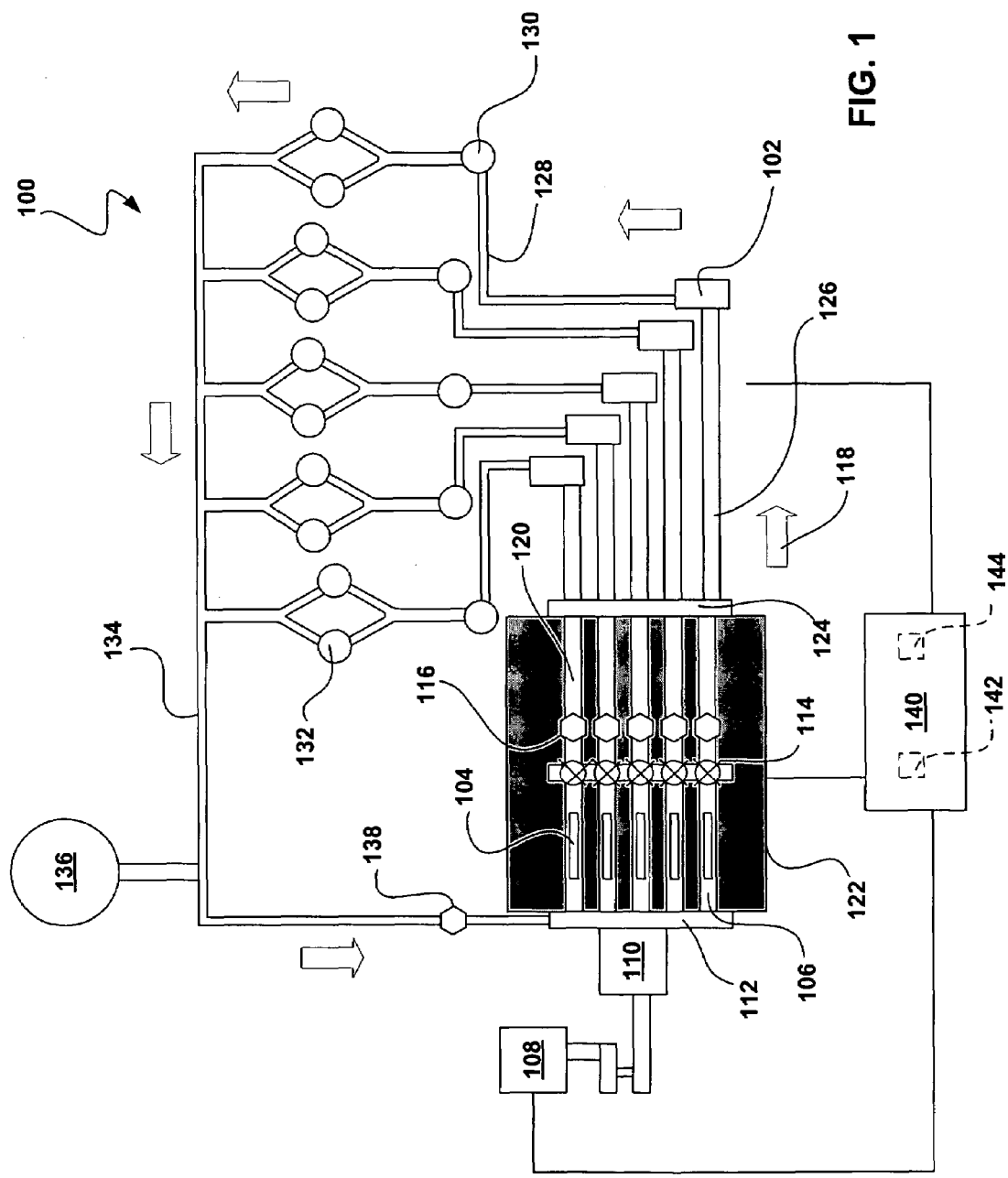
FIG. 1 illustrates a durability test apparatus having integrated particle counters according to one embodiment.

FIG. 1 illustrates a durability test apparatus 100 having one or more in-line particle counters 102. An implantable medical device 104 is deployed in a conduit 106, which may, for example, be a vascular graft or a mock artery fabricated of silicone. Motor 108 moves fluid from pump 110 by the action of metal bellows, rolling rubber bellows, a piston or the like. Motor 108 may include, for example, a hydraulic, electrodynamic, AC or servo drive system. From pump 110, fluid moves through manifold 112, where pressures being delivered to devices 104 are monitored. Manifold 112 may contain stopcocks or isolation valves (not shown) that allow conduits 106 and devices 104 to be isolated, removed, replaced, and/or inspected without draining the entire apparatus 100.

Stopcocks 114 may be disposed downstream of conduits 106 to allow the user to select which conduit(s) 106 are open and which are closed. Check valves 116, also known as bleed valves or one-way valves, allow fluid to flow along the path shown by arrow 118, while inhibiting or preventing backflow during diastole of pump 110 when a pulsatile flow is used for testing. Check valves 116 also help to control the rate of flow through elastomeric tubing 120. A tank 122, containing implantable device 104, conduit 106, stopcocks 114, check valves 116 and tubing 120, may be filled with a heated liquid, for example, to simulate body temperature.

Test fluid exits elastomeric tubing 120 through manifold 124 and is carried to particle counter 102 by tubing 126. Fluid leaving particle counter 102 is directed to tube 128 and through flow meter 130. Flow meter 130 helps to regulate the steady flow of fluid through particle counter 102. Filter 132 removes particles from the fluid and returns the filtered fluid to tube 134. For example, a deep convoluted filter that allows for rapid filtration at relatively low pressure, approximately 3 psi, may be used. Output from multiple particle counters 102 may alternatively be directed to a single filter 132. Capacitance tank 136 maintains a constant fluid volume in apparatus 100. Check valve 138 allows fluid to be recirculated back to pump 110, but prevents positive pressure in the direction opposite arrow 118 during the systolic phase of pulsatile pumping. Motor 108, particle counter 102 and controls for temperature, pressure, speed (cycle rate) and flow (located on or in tank 120) are controlled by a computer 140 that includes a microprocessor 142 and memory 144. Microprocessor 142 executes data acquisition and display software.

It will be appreciated that FIG. 1 teaches by way of example and not limitation. The number of system components may be increased or decreased with respect to what is shown. In one such example, sensors (not shown) providing optional alarm capabilities for temperature, mean pressure, pulsatile pressure, number of cycles, and speed may be incorporated into apparatus 100. In another example, a booster pump (not shown) may be inserted between capacitance tank 136 and check valve 138. The booster pump may accelerate test conditions where, for example, 400 million heartbeats may be replicated at a cycle rate ranging from about 50-6000 cycles/minute.

Figure 2:
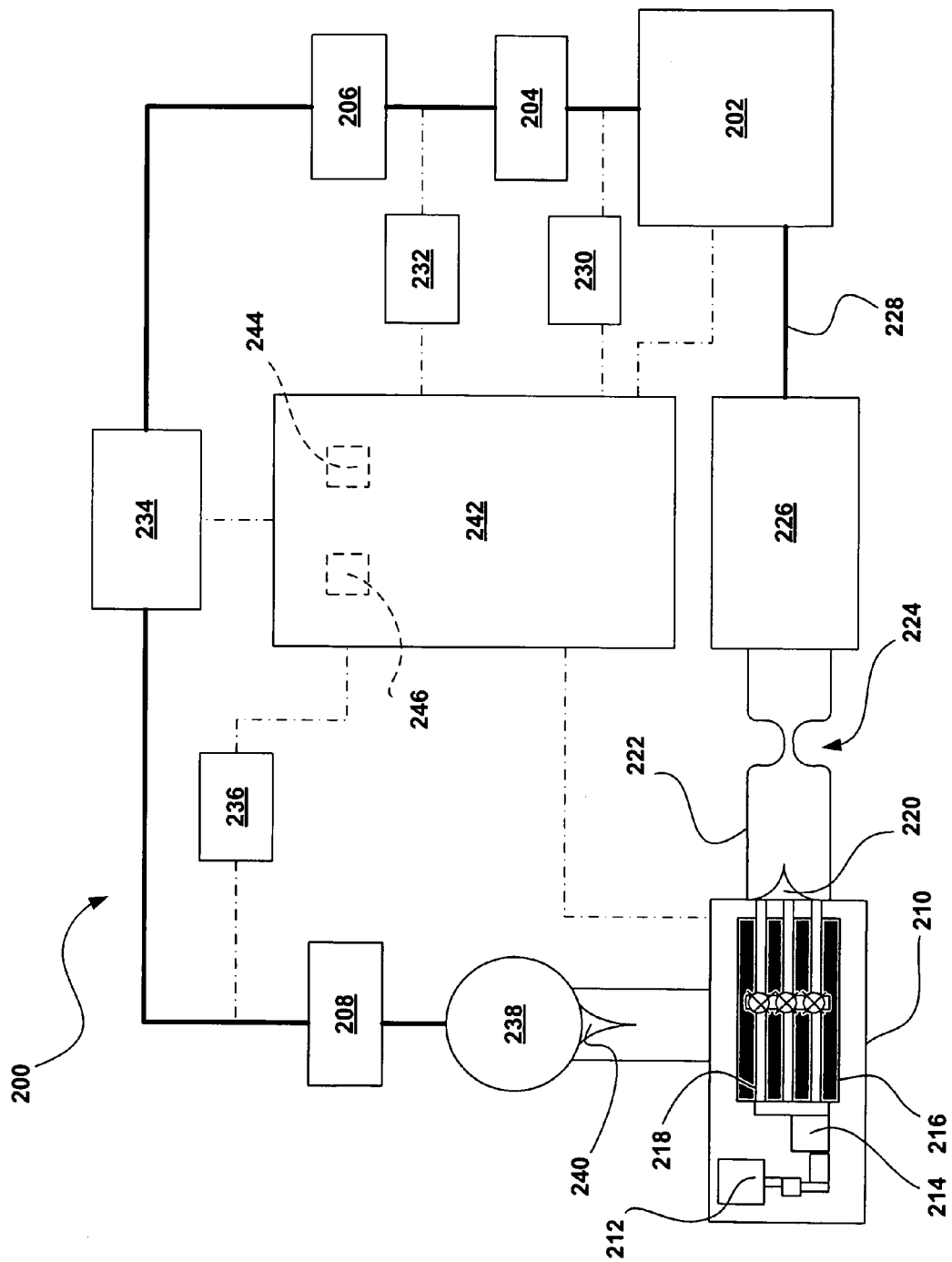
FIG. 2 illustrates a durability test apparatus having an integrated particle counter and a series of filters according to one embodiment.

FIG. 2 illustrates a durability test apparatus 200 having an integrated particle counter 202 and filters 204, 206, 208 in series. Filters 204, 206, 208 collect particles for further chemical and/or microscopic analysis and clarify fluids that may be recirculated. A housing 210 includes a motor 212, a pump 214, a tank 216 for a temperature bath, and at least one conduit 218 where conduit 218 may be the implantable device under test. Adjustable mounting plates within housing 210 allow for utilization and/or testing of conduits 218 of varying compliance, diameter and length. A one-way valve 220 (see also FIG. 1, 116) keeps fluid from returning to housing 210 during diastole of peristaltic pump 214. A chamber 222 collects fluid from all conduits 218. Chamber 222 contains a restrictor 224 that regulates pressure and flow. Following a pulsatile to steady flow transition area 226 where an adjustable chamber houses tubing of sufficient volume (i.e., length/diameter) and compliance to mitigate wave properties associated with a pulsatile flow, the fluid exits into tubing 228 which leads to particle counter 202. Fluid exiting particle counter 202 encounters filter 204. A pressure transducer 230 is used to monitor the fill volume of filter 204, so that it may be changed at an appropriate time. Filter 206 is a back-up for filter 204, used primarily in cases of failure or removal (e.g. changing) of filter 204.

Pressure transducer 232 monitors the fill volume of filter 206. An auxiliary pump 234 may be integrated with apparatus 200 to overcome reductions in flow rate primarily due to the presence of filters. Filter 208 removes possible contaminants from upstream components (e.g. auxiliary pump 234). Pressure transducer 236 monitors the fill volume of filter 208. A reservoir 238 presents fluid to pump 214 during diastole. A one-way valve 240 keeps reservoir 238 from being refilled from pump 214 during systole. A computer 242 includes a microprocessor 244 and memory 246.

Microprocessor 244 controls components within housing 210, particle counter 202, auxiliary pump 234, and pressure transducers 230, 232, 236. Parameters controlled by microprocessor 244 include, for example, stroke volume, frequency, temperature, pressure, total cycles, particle counter source intensity, and auxiliary pump use. It will be appreciated that microprocessor 244 may control components either directly or indirectly, for example, through relays, amplifiers, controller or driver circuitry, and/or other means.

In one embodiment, fluid contacting a single device 104 in a single conduit 106 may be analyzed by the particle counter 102, 202. Alternatively, multiple devices 104 in multiple conduits 106 may be monitored and fluid from only one or a few conduits 106 analyzed by one or more particle counters 102, 202. Fluid from the remaining (unmonitored) devices 104 may be filtered to confirm that particle shedding is consistent. In yet another embodiment, an apparatus 100, 200 directs fluid exiting from conduits 106 sequentially through particle counter 102, 202 and into filter 132, 204, 206, 208. A discontinuous set of data for each device 104 may be collected by sequential sampling, with increased sampling rates approximating continuous monitoring.

The apparatuses of the above embodiments advantageously integrate one or more in-line particle counters. In-line particle counters improve precision and accuracy of particle measurements relative to measurements made by extracting fluid from a test apparatus and analyzing the fluid with an off-line particle counter. Off-line methods increase sample handling and introduce sources of error, such as new surfaces for particles to contact and stick to, settling due to gravity, and pressure changes related to drawing and dispensing samples that may break up large particles.

Particle counters suitable for integration with the apparatuses described herein include those with flow cells that allow for particle counting on a continuous basis. Several suitable particle counters are commercially available including Coulter counters, which measure changes in electrical resistance produced by non-conductive particles suspended in an electrolyte, and laser light obfuscating counters. For example, the PC2400D™ is a suitable laser light obfuscating particle counter produced by ChemTrac Systems, Inc. of Norcross, Ga. The PC2400D™ includes a flow cell with dimensions of about 1 mm×1 mm at 2 micron resolution with a flow rate of 100 mL/min. Most particle counters require a relatively narrow range of steady state flows ranging from about 60 to 100±1 mL/min. An apparatus can, however, be adapted to divert the appropriate amount of flow from tubing 126 to particle counter 102, 202 then recombine the fluid before filter 132, 204, 206, 208. The fluid analyzed by the particle counter is considered representative of the bulk fluid and a quantitative estimate of particles in the bulk fluid is made by multiplying the measured value (counts per mL) by the total volume that would have passed through the counter had the by-pass loop not been in place. The size resolution of a particle counter is typically between about 0.2-1000 microns, and more typically between about 2-250 microns. Data may be binned according to particle size as selected by a user.

Given the narrow range of steady state flows required by particle counters, tests utilizing a pulsatile flow to replicate a heartbeat require that the flow be converted to a steady flow before the fluid enters the particle counter. In the apparatuses described herein, check valves 116, 138, 212, 232, fabricated of stainless steel and polytetrafluoroethylene (PTFE), isolate housing 210 and components therein. Positive pulsatile pressure is mitigated in pulsatile to steady flow transition area 218 that includes an adjustable chamber that houses elastomeric tubing. Tubing of varying elasticity, lengths and/or diameters is incorporated in the adjustable chamber, where the length and/or diameter of the tubing is determined by the volume and elasticity needed to mitigate the wave properties of the pulsatile flow.

Although the apparatuses described herein are designed to accommodate pulsatile flows, they may be operated under conditions of steady flow when a suitable pump (e.g. centrifugal) is used.

Apparatus components that come into contact with the test fluid should be robust toward attritional degradation and substantially free of seams and/or protrusions that might trap particles shed from the device. Suitable materials include, for example, stainless steel, titanium and other metals, ceramics, glass, and polymers such as polyethylene, polytetrafluoroethylene (PTFE) (e.g., Teflon®), silicone rubber, natural rubber, polyurethane, Dacron®, polyvinyl chloride, polystyrene, nylon, natural rubber latex and combinations thereof.

EXAMPLE 1

Method of Using a Durability Test Apparatus

Incorporating a Particle Counter

In vitro testing of particle shedding from a coated stent is performed using a durability test apparatus incorporating an in-line particle counter as described above. All stents selected for testing should be finished, sterilized, clinical quality product. Cosmetic rejects or non-clinical devices may be used if the cause for rejection is not related to efficacy.

Protocol

The apparatus is equipped with one or more conduits of particular diameter, length and dynamic internal compliance specifications (See AAMI-ISO 25539-1 AM and 7198) that are matched to the stent to be tested. The apparatus is filled with fluid and operated for approximately 5 minutes without incorporating stents in the conduits to establish baseline interference. Following the completion of the blank run, fluid may be emptied from the apparatus and empty conduits may be replaced, using a clean technique, with conduits containing the coated stents to be tested. Stents are deployed into a conduit using manufacturer's recommendations for the implant site in a clean environment, such as a clean room or a portable glove box. The conduits are positioned in the device and subjected to conditions that mimic in vivo blood pressures, flow rates and temperatures. Pulsations may occur at normal heart rates of approximately 70 bpm, for example, or may be accelerated to higher rates to shorten the test duration. The apparatus is refilled with fluid and adjustments are made to attain the necessary frequency, pressure and flow. Fluid is analyzed to provide knowledge of the time course and size of particles shed from the stents. The test proceeds for a predetermined number of cycles, with filters being changed either at selected time intervals or when indicated by sensor alarms.

Data may be displayed in real-time or saved to memory for later viewing and evaluation. For example, data may be recorded in ASCII format, as counts per volume or counts per time increment, and displayed textually or graphically. Typical graphs of interest include time versus total number of particles (total concentration), cycle number versus total number of particles, time versus number of particles of a particular size (or narrow size range), and cycle number versus number of particles of a particular size (or narrow size range). Particle data collected as a function of time represents a time-dependent profile.

Time-dependent particle shed profiles may provide users with knowledge of how long an implantable or inter-dwelling device may be safely used; whether shedding is concurrent with structural fatigue; whether a device having multiple coatings sheds only one coating or multiple coatings; which coating begins the shedding process; which materials are prone to shedding large/small particles; and other useful information. It will be appreciated that chemical identification of shed particles may be performed after filtration and retrieval of the particles from the test fluid. Suitable techniques known in the chemical arts include, for example, infrared spectroscopy, X-ray diffraction, reactivity studies and the like.

The changes described above, and others, may be made in the apparatuses and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and apparatus, which, as a matter of language, might be said to fall there between.

What is claimed is:

1. An apparatus for determining a particle shed rate of an implantable medical device comprising:
    a pump that moves fluid in contact with the implantable medical device; and
    a particle counter, the particle counter collects data representative of a time-dependent particle shed profile of the implantable medical device;
    wherein the pump, the implantable medical device, and the particle counter are in fluidic communication; and
    wherein the pump applies pulsatile fluid pressure and there is a pulsatile to steady flow transition.

2. The apparatus of claim 1, wherein the pulsatile to steady flow transition comprises a length of tubing having sufficient volume and compliance to mitigate wave properties associated with pulsatile flow.

3. A method of determining a particle shed rate of an implantable medical device comprising:
    deploying the implantable medical device in a durability test apparatus;
    contacting fluid with the implantable medical device; and
    analyzing the fluid using an in-line particle counter by performing the steps of transitioning the fluid from a pulsatile flow to a steady flow and utilizing the particle counter to acquire data representative of a time-dependent particle shed profile of the implantable medical device.

4. A method of determining a time-dependent particle shed profile of an implantable medical device comprising:
    deploying the implantable medical device in a durability test apparatus;
    continuously cycling fluid through a medical device durability test apparatus,
    wherein the durability test apparatus has an in-line particle counter and an in-line filter; and
    analyzing the fluid with the particle counter over a period of time ranging from about 1 hour to 1 year;
    wherein the step of analyzing the fluid comprises the steps of transitioning the fluid from a pulsatile flow to a steady flow; and utilizing the particle counter to acquire data representative of a time-dependent particle shed profile of the implantable medical device over a period of time ranging from about 1 hour to 1 year.

* * * * *